(12) United States Patent
Cervantes

(10) Patent No.: US 7,353,946 B2
(45) Date of Patent: Apr. 8, 2008

(54) PROTECTIVE PACKAGING ASSEMBLY FOR MEDICAL DEVICES AND METHOD OF USING SAME

(75) Inventor: Marvin J. Cervantes, Santa Rosa, CA (US)

(73) Assignee: Medtronic Vascular, Inc., Santa Rosa, CA (US)

( * ) Notice: Subject to any disclaimer, the term of this patent is extended or adjusted under 35 U.S.C. 154(b) by 868 days.

(21) Appl. No.: 10/843,609

(22) Filed: May 11, 2004

(65) Prior Publication Data

US 2005/0252805 A1    Nov. 17, 2005

(51) Int. Cl.
*A61B 17/06* (2006.01)

(52) U.S. Cl. .................. 206/428; 206/364; 206/1.5; 220/281

(58) Field of Classification Search .......... 206/438, 206/363–366, 571, 1.5, 63.3, 550; 623/1.11; 220/281, 4.04, 836, 913; 215/305, 295, 216; 604/192

See application file for complete search history.

(56) References Cited

U.S. PATENT DOCUMENTS

| | | | | |
|---|---|---|---|---|
| 4,335,756 A * | 6/1982 | Sharp et al. | ................... | 138/89 |
| 4,480,762 A * | 11/1984 | Thomas | ...................... | 215/273 |
| 4,928,830 A * | 5/1990 | Brewer | ...................... | 206/570 |
| 4,950,227 A | 8/1990 | Savin et al. | ............... | 623/1.12 |
| 5,133,454 A * | 7/1992 | Hammer | ..................... | 206/364 |
| 5,280,809 A * | 1/1994 | Tive | .......................... | 138/89.3 |
| 5,391,172 A | 2/1995 | Williams et al. | ........... | 623/1.11 |
| 6,159,229 A | 12/2000 | Jandeusee et al. | .......... | 606/198 |
| 6,342,066 B1 | 1/2002 | Toro et al. | ................... | 623/1.11 |
| 6,595,362 B2 * | 7/2003 | Penney et al. | .............. | 206/364 |
| 6,612,450 B1 * | 9/2003 | Buono | ......................... | 215/228 |
| 6,896,141 B2 * | 5/2005 | McMichael et al. | ......... | 206/571 |
| 2001/0012959 A1 | 8/2001 | Blaeser et al. | ............. | 623/1.11 |

* cited by examiner

*Primary Examiner*—Mickey Yu
*Assistant Examiner*—Steven A. Reynolds

(57) ABSTRACT

A protective packaging system for a medical device includes a housing and an end cap. The housing surrounds the distal portion of a catheter bearing a medical device so that the device is suspended in a protective chamber. The end cap holds the housing closed. Another embodiment of the invention provides a method for removing a catheter and medical device from the packaging system.

22 Claims, 5 Drawing Sheets

PROTECTIVE PACKAGING ASSEMBLY FOR MEDICAL DEVICES AND METHOD OF USING SAME

FIELD OF THE INVENTION

This invention relates generally to packaging of medical devices, and particularly to methods and an assembly for protecting medical devices used to treat cardiovascular disease during handling.

BACKGROUND OF THE INVENTION

Cardiovascular disease, including atherosclerosis, is a leading cause of death in the U.S. A number of methods and devices for treating coronary heart disease have been developed, some of which are specifically designed to treat the complications resulting from atherosclerosis and other forms of coronary arterial narrowing.

One method for treating atherosclerosis and other forms of coronary narrowing is percutaneous transluminal coronary angioplasty, hereinafter referred to as "angioplasty" or "PTCA". Many heart disease patients undergo angioplasty, some repeatedly.

The objective of angioplasty is to enlarge the lumen of the affected coronary artery by radial hydraulic expansion. This is generally accomplished by inflating a balloon within the narrowed lumen of the affected artery. Radial expansion of the coronary artery may occur in several different dimensions, and is related to the nature of the plaque. Soft, fatty plaque deposits are flattened by the balloon, while hardened deposits are cracked and split to enlarge the lumen. The wall of the artery itself may also be stretched as the balloon is inflated.

With simple angioplasty, the balloon is threaded through the artery with a catheter and inflated at the place where the blood vessel is blocked. After the procedure, the balloon is removed. Following simple angioplasty alone, arteries frequently close up again or re-narrow. This narrowing is known as restenosis.

To reduce the risk of restenosis, a stent may be inserted during angioplasty. The stent may be used to maintain the internal lumen of the artery after the balloon is removed. The use of a stent may significantly reduce the risk of restenosis. The stent is designed to support plaque damaged arterial walls after a blockage has been removed.

Typically, if restenosis occurs with a stent, the physician may insert highly radioactive pellets into the artery to help prevent further clogging. This radiation therapy can halve the risk of restenosis but presents all the risks associated with radiation therapy.

Blood vessel wall injury when the stent is implanted is one cause of restenosis. The area around the stent becomes inflamed and new cells form scar tissue. The arterial walls may become so thick in some instances that they protrude into the mesh of the stent. In such cases, a further angioplasty may be performed, and a new stent may be placed inside the existing one. If restenosis continues, the eventual alternative may then be bypass surgery.

Alternatively, a coated stent may be inserted during the angioplasty. Such a coated stent may eliminate the need for repeat angioplasties and could spare some patients the trauma, risk and prolonged recovery associated with heart bypass surgery.

The stent may be coated, for example, with rapamycin analogs or rapamycin derivatives. This drug is used to prevent organ rejection in kidney transplants. It stops new cells from forming without impairing the healing of the vessel. It also dampens inflammation and has antibiotic properties.

In clinical studies, patients who have received coated stents exhibited a substantially reduced re-narrowing and re-blockage of arteries.

However, because the coating of the stent comprises a therapeutic drug, coated stents present problems associated with drug administration. For example, for a drug to be administered effectively, the integrity of the drug's effective dosage must be maintained. Additionally, contamination of the drug should be avoided. Moreover, certain drugs require controlled conditions to maintain efficacy, including exposure to air, moisture, light etc.

Currently, stents may be protected with a sheath that closely surrounds the stent. With a coated stent, this protective sheath may damage the coating while the sheath is being placed on, or removed from, the stent. If the sheath is too tight, the coating may stick to the sheath rather than the stent. If the sheath is removed improperly, some of the coating may also be removed. In any of these cases, the dosage of the drug will be reduced.

In addition, stents may be sterilized or otherwise treated prior to deployment. Such treatments may also damage the coating.

It would be desirable therefore to provide a protective assembly for stents, coated stents, angioplasty balloons, and other medical devices used to treat restenosis that overcomes the above limitations.

SUMMARY OF THE INVENTION

One embodiment of the present invention provides a system for packaging a treatment device comprising a housing that surrounds the distal portion of a catheter carrying a treatment device. The treatment device is suspended in a protective chamber. The housing comprises two portions rotatably connected to each other so that the housing may be opened and closed. When the housing is in a closed configuration, an end cap is slipped over the distal portion of the housing. The end cap has an interior surface that mates with the end portion of the housing, and opposing protrusions extending from the cap surface adjacent to the distal end of the end cap. When the protrusions are pressed, the opening of the cap is reconfigured to allow the cap to be disengaged from the housing and removed.

Another embodiment of the present invention provides a method for removing a treatment device from a packaging system. The packaging system includes a housing enclosing the distal portion of a catheter and the treatment device, and an end cap mated with the distal portion of the housing. To open the packaging system, the end cap is flexed, causing the shape of the opening of the end cap to be altered. The end cap is then removed and the housing is opened by rotating one portion of the housing in relation to the other portion to an open configuration. The catheter and treatment device are then removed from the opened housing.

DETAILED DESCRIPTION

Throughout this specification, like numbers refer to like structures.

Figure 1:
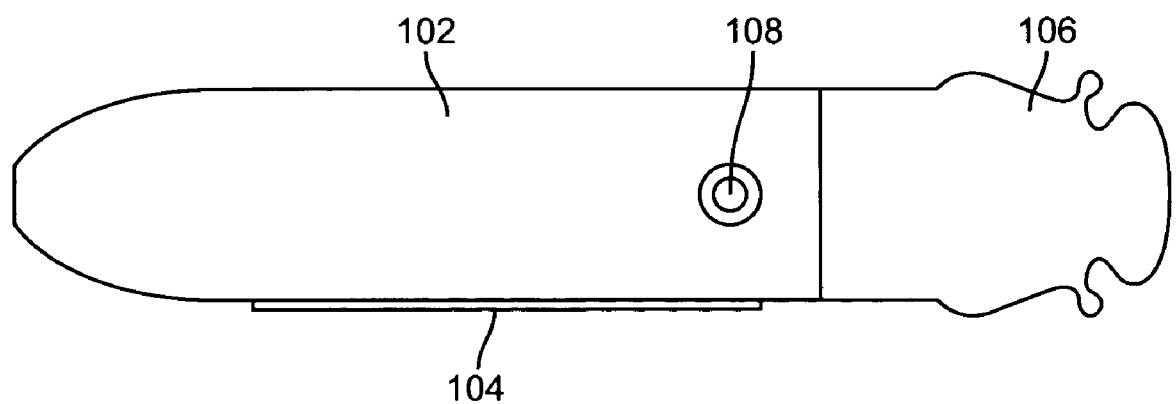
FIG. 1 is a schematic view of one embodiment of a packaging system for a treatment device comprising a housing and an end cap in a closed configuration in accordance with the present invention.

Referring to the drawings, FIG. 1 is a schematic view of a packaging system 100 for a medical device. The packaging system 100 includes a housing 102 and an end cap 106. Housing 102 comprises two portions attached to each other by a hinge 104, and having a controlled environment port 108. End cap 106 slips over the distal portion of the housing 102 and seats firmly against it. The function of the end cap 106 is to maintain the housing 102 in a closed configuration.

Packaging system 100 may be used to protect any of a variety of medical devices that are carried on a catheter including stents, coated stents, angioplasty balloons, balloon and stent combinations, electronic components, sensors and monitoring devices. Many such devices are fragile, sensitive to oxygen, light, or moisture, and must be delivered to the patient sterile. Drug-eluting coated stents are particularly vulnerable because, in addition to the integrity of the stent, the efficacy of the drug must be maintained.

Stents used in accordance with the present invention comprise alloys of metals such as stainless steel, nickel, titanium, and cobalt. Drug-eluting coatings may comprise any suitable therapeutic agent for delivering therapy to a target site, and may include any suitable substance within which such therapeutic agents may be dispersed. The coating may be biodegradable, or porous and non-biodegradable. In an alternative embodiment, a biodegradable stent may have the therapeutic agent impregnated within the stent matrix. The therapeutic agent may comprise one or more of the following: thrombin inhibitors, antithrombogenic agents, thrombolytic agents, fibrin, fibrinolytic agents, vasospasm inhibitors, calcium channel blockers, vasodilators, antihypertensive agents, antimicrobial agents, antibiotics, inhibitors of surface glycoprotein receptors, antiplatelet agents, antimitotics, microtubule inhibitors, antisecretory agents, actin inhibitors, remodeling inhibitors, anti metabolites, antiproliferatives, anticancer chemotherapeutic agents, anti-inflammatory steroid or non-steroidal anti-inflammatory agents, immunosuppressive agents, growth hormone antagonists, growth factors, dopamine agonists, radiotherapeutic agents, peptides, proteins, enzymes, extracellular matrix components, collagen, inhibitors, free radical scavengers, chelators, antioxidants, antipolymerases, antiviral agents, photodynamic therapy agents, gene therapy agents, including antisense oligonucleotides, ribozymes, genes carried by viral vectors (retro, adeno, adenoassociated), and non-viral systems (plasmid, cationic, lipid materials), vascular cell promoters, other biologic agents, conjugates or combinations thereof.

Figure 2:
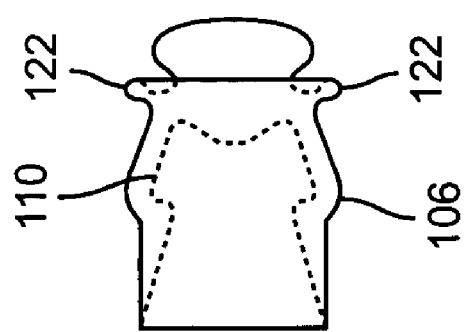
FIG. 2 is a schematic view of the embodiment of the packaging system shown in FIG. 1 in an open configuration with a catheter and stent in accordance with the present invention.
Figure 2:
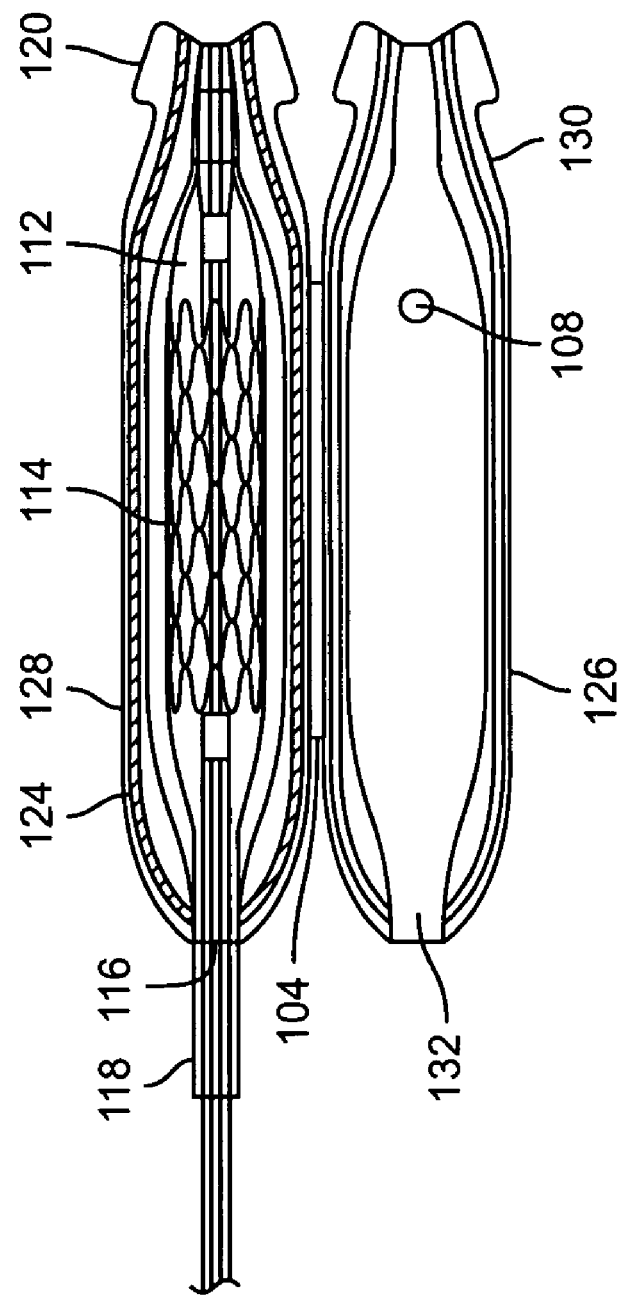

FIG. 2 is a schematic view of the packaging system 100 in an open configuration with a stent 114 mounted on the distal portion of a catheter 118. Catheter 118 may further comprise an expandable balloon portion. The interior of the housing 102 forms a chamber 112 that surrounds the stent 114. The end cap 106 has been withdrawn from the distal end portion of the housing 102, and a first portion 126 of housing 102 has been rotated about hinge 104 in relation to a second portion 128 of housing 102, so that the housing 102 is in an open configuration.

In one embodiment of the invention, housing 102 is rigid so that the medical device is protected from bending, or being touched during handling. Housing 102 may be composed of any rigid or semi-rigid, biocompatible, polymeric material such as polyurethane, polyethylene, high-density polyethylene, nylon, polytetrafluroethylene (PTFE), or mixtures thereof. During the manufacturing process, the housing 102 is formed by a process of casting, extrusion, injection, or blow-molding the polymeric material to form the needed shape.

In one embodiment of the invention, the distal portion of the housing 102 has a tapered portion 130, and at the distal end, forms a broader tail section 120. The inner surface 110 of the end cap 106 has a complementary configuration so that when seated over the distal end of the housing 102, the end cap adheres tightly to the housing 102. The end cap 106 maintains the housing 102 in a closed configuration when the end cap 106 is in place. In one embodiment of the invention, an airtight seal is formed between the edges of the first portion 126 and the second portion 128 of housing 102. In addition, there is a sealing member 116 that surrounds the catheter 118. In one embodiment of the invention, sealing member 116 forms a gas impermeable seal. Thus, when the housing 102 is closed, a controlled environment may be maintained within the housing 102.

In one embodiment of the invention, there is a liner 124 adjacent to the inner surface of the housing 102. The liner is selected to maintain an environment that is optimal for the stability of the medical device. If the medical device is a stent with a drug-eluting coating, the liner may comprise an opaque material such as foil in order to protect the drug from light. If the medical device is sensitive to moisture, the liner may comprise an adsorbent material. If the medical device includes a radioactive isotope, the liner may be a material that is impenetrable by radiation. In one embodiment of the invention, the liner comprises Tyvek®, a porous material composed of high-density polyethylene fibers. Tyvek® is resistant to penetration by bacteria, spores, and other contaminating microorganisms, and maintains a sterile environment for long periods of time. Consequently, the medical device may be enclosed in the Tyvek® liner and sterilized using ethylene oxide, gamma radiation, electron-beam radiation, steam, plasma/hydrogen peroxide, or any other appropriate sterilant. The medical device will be sterile as long as it remains within the Tyvek® liner.

The controlled environment port 108 may be used to change the atmosphere within the housing 102. For example, controlled environment port 108 may be used draw a vacuum or to inject an inert gas such as nitrogen or argon to prevent oxidation of polymers or therapeutic agents that are components of the medical device. Controlled environment port 108 could also be used to inject a gaseous sterilant such as ethylene oxide to effect sterilization of the medical device. Alternatively, controlled environment port 108 may be used in a combination of processes, for example, first to inject and exhaust a gaseous sterilant, and then to inject an inert gas. Once the atmosphere inside the housing 102 is established, it will remain unchanged until housing 102 is opened.

One embodiment of the invention includes an indicator on housing 102 that indicates whether the device inside has been sterilized. Many such indicators are widely known and used in the manufacturing of medical products.

Figure 3:
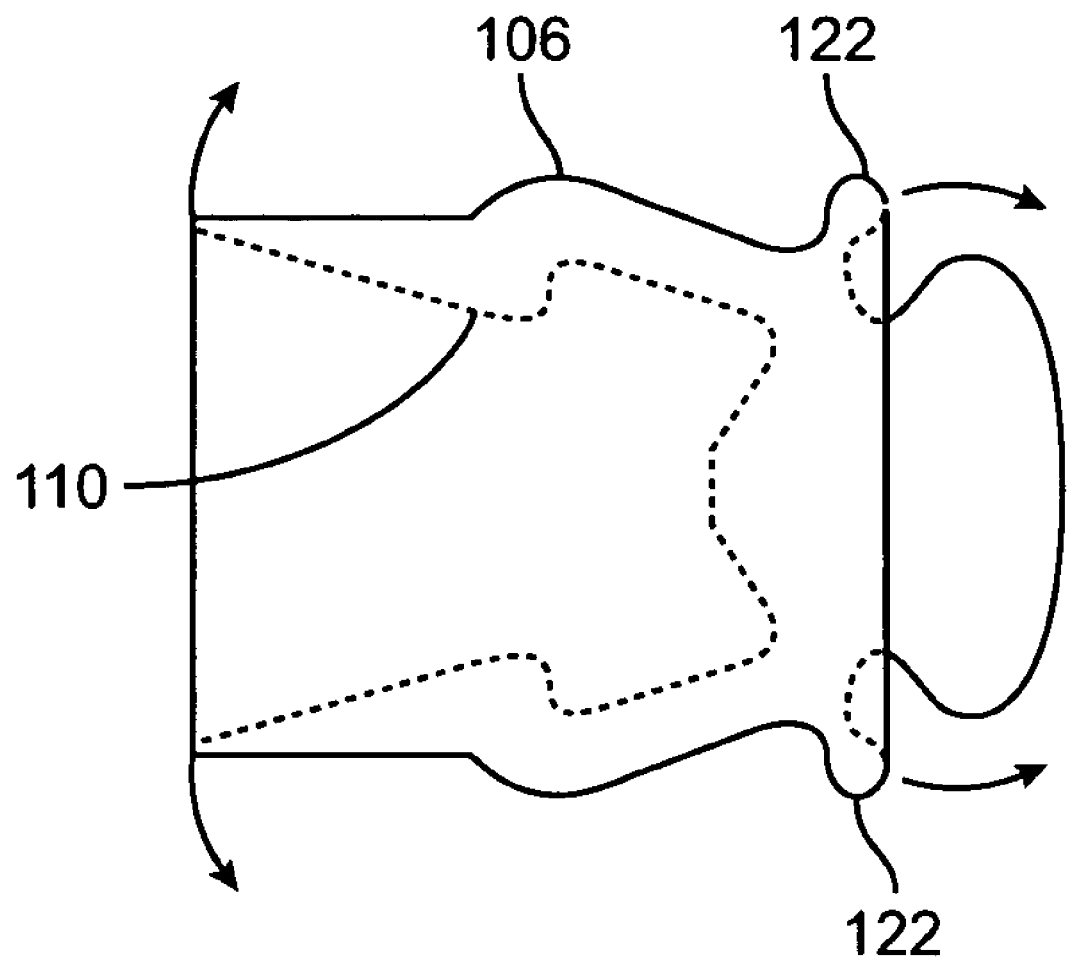
FIG. 3 is a cross sectional view of the end cap showing how the shape of the opening is altered by pressing on the protrusions on the distal surface, in accordance with one embodiment of the invention.

FIG. 3 is a cross sectional view of end cap 106. End cap 106 is closed at the distal end but has an opening at the proximal end. End cap 106 comprises a biocompatible polymeric material such as polyurethane, polyethylene, nylon, polytetrafluroethylene (PTFE), or combinations thereof. In one embodiment of the invention, end cap 106 is flexible, but maintains it shape. The interior surface 110 of end cap 106 is shaped so that it is complementary to the tapered portion 130 and the tail section 120 of housing 102. Thus when the distal end of housing 102 is inserted into the proximal opening of end cap 106, and gentle pressure is applied to end cap 106, the walls of the end cap 106 will flex and allow the end portion 120 of housing 102 to pass into the matching portion of cap 106. Once firmly seated about the distal end portion of housing 102, end cap 106 holds housing 102 in a closed and sealed configuration.

In one embodiment of the invention, end cap 106 has two opposing protrusions 122 extending from the cap surface adjacent to the distal end of the end cap 106. The protrusions may be flexed toward the distal surface of end cap 106 as indicated by the arrows adjacent the protrusions 122 in FIG. 3. Flexing the protrusions distally causes the walls of end cap 106 adjacent to the protrusions to flex outward as shown in FIG. 3 by the arrows adjacent to the proximal, open end of end cap 106. As the walls of end cap 106 flex outward, they disengage from the surface of housing 102 allowing end portion 120 to exit the complementary portion of end cap 106. The end cap 106 may then be pulled away from the distal end of housing 102.

Figure 4A:
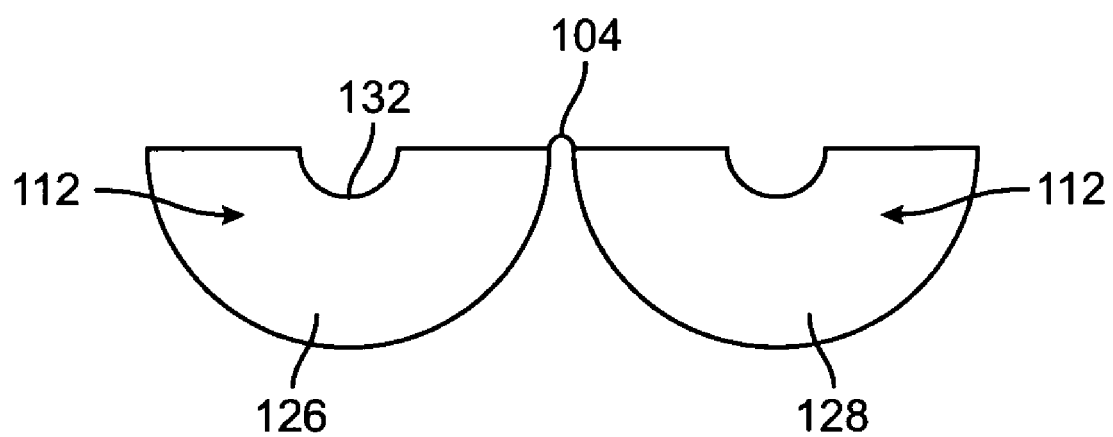
FIG. 4A is an end view of the housing portion of the packaging system in an open configuration in accordance with the present invention.

FIG. 4A is an end view of housing 102 in an open configuration. Housing 102 forms a chamber 112 that surrounds and protects the medical treatment device. In one embodiment of the invention, housing 102 includes a groove 132 at the proximal and distal ends of the chamber 112. In this embodiment, a medical device that is carried on a catheter may be suspended in the chamber 112 by laying the distal portion of the catheter 118 (FIG. 1) in the groove 132. When the first portion 126 and the second portion 128 of housing 102 are in a closed configuration about hinge 104, the treatment device is completely enclosed within chamber 112. By this means, the treatment device is protected from bumping or touching the inner wall of chamber 112.

Figure 4B:
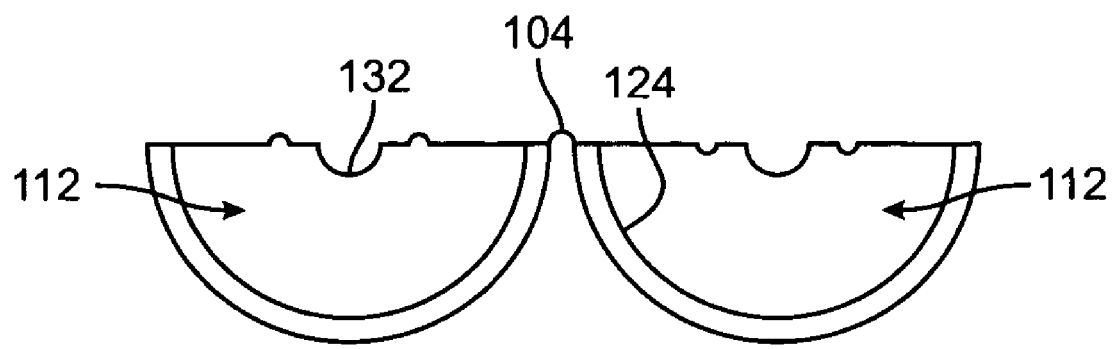
FIG. 4B is an end view of the housing portion of the packaging system with a liner in an open configuration in accordance with the present invention.

FIG. 4B is an end view of housing 102 in an open configuration with a liner 124. When the first and second portions 126 and 128 are in a closed configuration, a treatment device suspended from a catheter in chamber 112 is enclosed within the liner.

Figure 5:
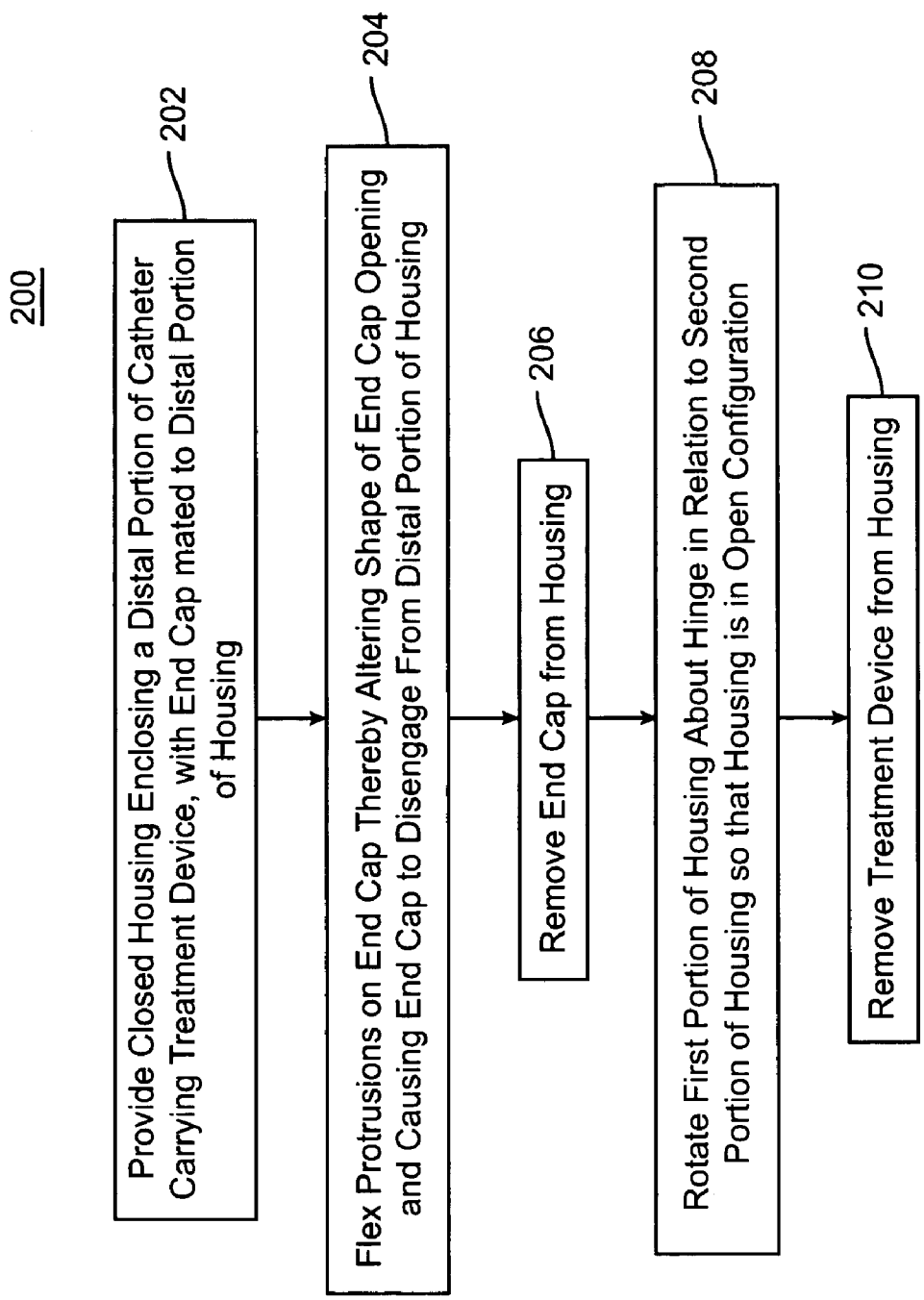
FIG. 5 is a flow diagram of a method for removing a treatment device from the packaging in accordance with the present invention.

Another embodiment of the invention includes a method 200 for removing a medical treatment device from the packaging system 100, as is illustrated in a flow diagram in FIG. 5. The method 200 begins at block 202 wherein a medical treatment device mounted on a catheter is provided within a closed housing 102 and having an end cap 106 in place over the distal portion of the housing. The device may be a stent, a coated stent, an angioplasty balloon, or any other fragile device that must be delivered sterile to the patient. The flexible protrusions on the end cap 106 are flexed toward the distal surface of the end cap as indicated in block 204. This action causes the opening in the proximal end of the end cap to change shape. As a result, the end cap disengages from the distal portion of the housing, and the end cap is removed from the housing as indicated in block 206. Next, the first portion of the housing is rotated about the hinge in relation to the second portion of the housing, until the housing is in an open configuration, as indicated in block 208. The treatment device is then gently removed from the housing as indicated in block 210, and delivered to the patient using appropriate surgical technique.

While the invention has been described with reference to particular embodiments, it will be understood by one skilled in the art that variations and modifications may be made in form and detail without departing from the spirit and scope of the invention.

What is claimed is:

1. A system for packaging a treatment device comprising:
   a housing to receive a distal portion of a catheter carrying a treatment device and to suspend the device in a protective chamber, the housing including a first portion rotatably attached to a second portion to allow rotation between an open and closed position, and
   a flexible end cap including an opening formed therein and an interior surface to mate with an end portion of the first and second housing portions in the closed position, the end cap including opposing protrusions extending from a cap surface adjacent a distal end of the end cap, wherein when the protrusions are pressed, a shape of the opening is reconfigured to allow removal of the end cap from the end of the housing.

2. The system of claim 1 wherein the end portion of the housing includes a narrow portion and a tail portion extending radially outward from the narrow portion, the inner surface of the end cap having a configuration complementary to narrow portion and the tail portion.

3. The system of claim 1 further comprising a controlled environment port.

4. The system of claim 1 further comprising at least one sealing member that forms a gas impermeable seal between the catheter and the housing.

5. The system of claim 4 wherein the sealing member maintains an inert gas within the interior of the housing.

6. The system of claim 4 wherein the sealing member maintains a reduced pressure within the interior of the housing.

7. The system of claim 1 wherein the housing comprises a polymeric material selected from a group consisting of polyurethane, polyethylene, high-density polyethylene, nylon, polytetrafluroethylene and combinations thereof.

8. The system of claim 1 wherein the treatment device is a stent.

9. The system of claim 8 wherein the stent is disposed upon an expandable balloon member.

10. The system of claim 8 wherein the stent is a self-expanding stent.

11. The system of claim 8 further comprising a coating on at least a portion of the stent.

12. The system of claim 11 further comprising at least one therapeutic agent dispersed within the coating.

13. The system of claim 11 further comprising at least one biologic agent dispersed within the coating.

14. The system of claim 11 further comprising at least one radiotherapeutic agent dispersed within the coating.

15. The system of claim 11 wherein the housing prevents damage to the coated portion of the stent during handling.

16. The system of claim 1 further comprising a gas permeable liner disposed about the inner surface of the housing.

17. The delivery system of claim 16 wherein the gas permeable liner comprises high-density polyethylene fibers.

18. The delivery system of claim 17 wherein the stent is sterilized using a sterilant selected from the group consisting of ethylene oxide, gamma radiation, electron-beam radiation, steam and chemicals.

19. A method for removing a treatment device from a packaging system, the method comprising:
- providing a closed housing enclosing a distal portion of a catheter carrying a treatment device, and an end cap mated to a tail portion of the housing;
- flexing said end cap and thereby altering a shape of an end cap opening;
- removing the end cap from the housing while the shape of the opening is altered;
- opening first and second portions of the housing to allow removal of the distal portion of the catheter carrying the treatment device.

20. The method of claim 19 wherein flexing said end cap comprises pressing opposing protrusions of the end cap.

21. The method of claim 19 wherein altering the shape of the end cap opening allows the removal of the end cap from the tail portion of the housing.

22. The method of claim 19 wherein opening the first and second portions of the housing comprises rotating a first portion of the housing in relation to a second portion of the housing to an open configuration.

* * * * *